United States Patent [19]
Wright et al.

[11] Patent Number: 5,751,421
[45] Date of Patent: May 12, 1998

[54] NEAR INFRARED SPECTROMETER USED IN COMBINATION WITH A COMBINE FOR REAL TIME GRAIN ANALYSIS

[75] Inventors: Steven L. Wright; C. Fred Hood, both of Johnston, Iowa

[73] Assignee: Pioneer Hi-Bred International, Inc., Johnston, Iowa

[21] Appl. No.: 807,661

[22] Filed: Feb. 27, 1997

[51] Int. Cl.$^6$ .................... G01J 3/28; A01F 12/00
[52] U.S. Cl. ................................ 356/328; 460/7
[58] Field of Search ............ 356/402–411, 330–334, 356/326, 328; 250/226, 339.12; 56/10.2 R; 460/4, 6, 7

[56] References Cited

U.S. PATENT DOCUMENTS

| | | |
|---|---|---|
| 3,597,616 | 8/1971 | Brunton et al. |
| 4,040,747 | 8/1977 | Webster |
| 4,253,766 | 3/1981 | Funk |
| 4,260,262 | 4/1981 | Webster |
| 4,463,261 | 7/1984 | Bowman |
| 4,560,275 | 12/1985 | Goetz ................ 250/339.12 |
| 4,806,764 | 2/1989 | Satake |
| 4,925,305 | 5/1990 | Erickson |
| 4,997,280 | 3/1991 | Norris |
| 5,132,538 | 7/1992 | Norris |
| 5,239,180 | 8/1993 | Clarke ................ 356/407 |
| 5,241,178 | 8/1993 | Shields |
| 5,308,981 | 5/1994 | Perten |
| 5,327,708 | 7/1994 | Gerrish ................ 56/10.2 R |
| 5,406,084 | 4/1995 | Tobler et al. |
| 5,517,302 | 5/1996 | Stearns et al. ........... 356/326 |

FOREIGN PATENT DOCUMENTS

1467470 A1  3/1989  U.S.S.R.

OTHER PUBLICATIONS

Rosenthal, "Characteristics of Non–Destructive Near–Infrared Instruments for Grain and Food Products" 1986 Meeting Japan food Science Institute.

G. Sinnaeve et all, *The Use of Near Infrared Spectroscopy for the Analysis of Fresh Grass Silage*, 1994, pp. 79–84, NIR Publications.

P. Dardenne et al., *Evaluation of NIT for Predicting Fresh Forage Quality*, pp. 277–283 No Date.

P. Dardenne et al., *Fresh Forage Analysis by Near Infrared Spectroscopy*, pp. 531–536 No Date.

Primary Examiner—K. Hantis
Attorney, Agent, or Firm—Zarley, McKee, Thomte, Voorhees, & Sease

[57] ABSTRACT

An apparatus and method for combining NIR spectography with a combine for measuring major constituents of harvested grain in real time includes a monochromator having no moving optical parts. The monochromator includes a fixed diffraction grating and a photodiode collector comprised of a plurality of photodiodes. A radiation source irradiates a grain sample while a bundle of fiber optic strands transmits the reflected radiation to the diffraction grating. By analyzing the intensities and wavelengths of the reflected radiation at the photodiode collector, the presence and amount of major constituents of the harvested grain can be determined. The present invention may be used on a research combine along with the conventional instrumentation which measures the weight, moisture, and volume of grain harvested in a test plot.

24 Claims, 5 Drawing Sheets

NEAR INFRARED SPECTROMETER USED IN COMBINATION WITH A COMBINE FOR REAL TIME GRAIN ANALYSIS

BACKGROUND OF THE INVENTION

1. Field of the Invention

The present invention relates to instruments for measuring constituents of harvested agricultural products. More particularly, though not exclusively, the present invention relates to a method and apparatus using near infrared spectrometers in combination with a combine for real time grain analysis.

2. Problems in the Art

In the field of agriculture, it is important to analyze agricultural products such as grain to determine the amount of major constituents in the grain. This is particularly important when developing hybrid species of crops.

One prior art method of analyzing grain and other agricultural products, is using near infrared spectroscopy (NIR). NIR is a well established technique for detecting both chemical and physical properties of various materials. NIR provides an accurate and inexpensive method to analyze agricultural materials such as grain. Major constituents that can be detected by using NIR include moisture, protein, oil, starch, amino acids, extractable starch, density, test weight, and any other constituents or properties that are of commercial value.

There are various types of devices used for NIR. In general, these devices include light sensors in conjunction with light sources which are used with any number of measuring devices. In optical spectrometers, the incident light from a light source is passed through a monochromator, which can be a filter or set of filters, a diffraction grating, or a prism whose angular displacement relative to the incoming light can be closely correlated with the single wavelength, or narrow band of wavelengths (which it sends on to the light sensor). The light sensor is selected so that its spectral responses match the wavelength of interest. The angular motion of the prism or diffraction grating can be mechanized so that a given spectrum is scanned at a known rate over a known time interval. Such a device is referred to as a scanning spectrometer. The wavelength of an observed peak can them be determined from the time counted from the start of a scan. Spectrometers may also be referred to as spectrophotometers when their spectral range extends between ultraviolet to infrared.

The constituent content of a grain sample is measured most accurately by prior art systems by grinding the sample of the grain to particulate form. The ground sample is then irradiated with near infrared light. The reflected radiation is detected at narrow band wavelengths in the NIR spectrum to obtain raw reflectance data of the sample. The data can be used to provide accurate measurements of the content of constituents of the grain samples. In many prior art systems, it is difficult to obtain accurate measurements of the grain constituents without first grinding the grain into particulate form.

Other prior art systems use scanning or oscillating spectrophotometric instruments. In such an instrument, a photo detector detects light energy which is scanned through a spectrum at a rapid rate. Such an instrument employs an optical grating which receives light through an entrance slit and disperses the light into a spectrum directed toward an exit slit. The optical grating is oscillated in order to rapidly scan the light transmitted through the exist slit through the spectrum dispersed by the grating. Another prior art instrument uses filters which are tilted as they pass through a light beam to scan the transmitted light through a spectrum. Either type of instrument, the oscillating optical grating or the tilt filter type can be operated over a spectrum covering near infrared to analyze agricultural products such as grain. Using an oscillating grating or tilting filter type of instrument, the user can measure the reflectivity of the sample at narrow wavelength increments to determine the constituent contents of a grain sample. To use an oscillating grating or tilting filter instrument, the narrow bandwidth light is transmitted through the exit slit used to illuminate the grain sample. The light reflected from the sample is detected by photo detectors and the resulting photo detector signal is used to determine the constituent contents of the sample. As the grating oscillates, the center frequency of the light that irradiates the sample is swept through the NIR spectrum. Light from the diffraction grating that is reflected by the sample is detected by the photo detector. As an alternative to detecting the energy reflected from the sample, the energy may be transmitted through the sample and detected after being transmitted through the sample. In addition, instead of irradiating the sample with the output from the spectrophotometer, the sample can be irradiated with constant wideband light and a reflected light being applied to the spectrophotometer.

If a grain sample is not ground, the light absorbence and reflectance varies considerably from sample to sample. This variation is caused by light scatter from the whole grain kernels and by the nonlinear surface reflectance effects. This variation makes it difficult to obtain accurate measurements from whole grain samples.

The spectrometers discussed require frequent calibration in order to generate accurate results. The calibrations must be performed frequently due to various dynamic factors including the change in light from a light source due to temperature sources. A typical method of calibrating a spectrometer is to replace the sample with a standard sample, for example, a white ceramic tile having high reflectance. The spectrometer scans the standard sample to provide standard values which are used to calibrate the spectrometer. While this calibration method works fine in a lab environment, it could be impossible, or at least impractical in the environment of a combine.

The spectrometers discussed above have several disadvantages. The spectrometers discussed are only suitable for use in a laboratory. Prior art methods of grain analysis have a major disadvantage resulting from the large amount of sample handling. The samples must be harvested, collected, bagged, labeled, dried, and finally sent to the NIR lab for constituent analysis. This excessive sample handling adds both cost and time to the analysis. A need can therefore be seen for an NIR instrument combined with a combine to automate the process of collecting an analyzing grain samples. Such a system would reduce the cost and time of the analysis. Such a system could provide plant breeders and grain farmers with real time information.

The main problem with an NIR instrument combined with a machine such as a combine is that prior art grain analysis instrumentation is very sensitive to mechanical vibrations. Scanning and oscillating spectrometers require very precise mechanical movements in order to obtain accurate results. The extreme vibrations found in the environment of a combine would result in damaged and inaccurate instrumentation equipment. In addition to the vibration, the combine environment is very dirty. The amount of dust and plant debris would severely effect the effectiveness of a conventional spectrometer.

3

Another problem with combining NIR instrumentation with a combine is that current NIR equipment requires a long time period for analysis. In the field of hybrid crop breeding, a large number of test plots are used to test hybrid plots. A typical test plot of hybrid corn, for example, is comprised of two rows of corn with a length of 17 ft. A research combine used to harvest the test plots goes through each test plot in approximately 15 seconds. A typical spectrometer used in a lab to analyze grain requires considerable more time than 15 seconds to analyze the grain sample. Therefore, even if convention NIR instrumentation is installed on a combine, the speed of harvesting test plots would be slowed down considerably by the slow speed of the NIR instrumentation.

A need can therefore be seen for NIR equipment in combination with a combine which could operate effectively in the environment of a combine which also is capable of analyzing grain samples in a short period of time.

FEATURES OF THE INVENTION

A general feature of the present invention is the provision of a method and apparatus for measuring constituents of harvested agricultural products in a combine which overcomes problems found in the prior art.

A further feature of the present invention is the provision of a method and apparatus for measuring constituents of harvested agricultural products on a combine which uses a monochromator with a photodiode array detector which has no moving optical parts and thus is more resilient to mechanical vibrations.

A further feature of the present invention is the provision of a method and apparatus of measuring constituents of agricultural products on a combine which is capable of measuring the constituents in a short time period.

Further features and advantages of the present invention include:

An apparatus and method of measuring the constituents of agricultural products on a combine which analyses grain samples while the grain is flowing through a portion of the combine to obtain a more accurate measurement.

An apparatus and method of measuring the constituents of agricultural products on a combine in which the monochromator is located within the cab of the combine and is connected to the optical sensor by a fiber optic connection.

An apparatus and method of measuring the constituents of agricultural products on a combine which can use either the reflectance or transmittance of radiation through the agricultural product.

An apparatus and method of measuring the constituents of agricultural products on a combine which measures the constituents in real time and stores the measurements for later use.

An apparatus and method of measuring the constituents of agricultural products on a combine which can be automatically calibrated.

An apparatus and method of measuring the constituents of agricultural products on a combine which senses the reflectance of the sample in more than one position in order to obtain higher accuracy.

These as well as other features and advantages of the present invention will become apparent from the following specification and claims.

SUMMARY OF THE INVENTION

The present invention relates to a method and apparatus for measuring constituents of harvested agricultural products on a combine. The invention uses near infrared spectography equipment which has no moving optical parts in order to withstand the vibrations found on a combine. A radiation source is used to irradiate a grain sample while the reflected radiation is transmitted by a fiber optic bundle to a monochromator located within or near the cab of the combine. The monochromator includes a diffraction grating or its equivalent which spreads the reflected light over a desired wavelength range over a photodiode collector which is comprised of a plurality of photodetectors. By analyzing the intensities of the reflected radiation, the major constituents of the grain can be determined. The apparatus of the present invention may be used with existing grain analysis equipment on a research combine which determines the grains weight, moisture content, volume, etc. of the grain. In this way, the process of harvesting and analyzing grain in a test plot can be fully automated.

DETAILED DESCRIPTION OF THE PREFERRED EMBODIMENT

The present invention will be described as it applies to its preferred embodiment. It is not intended that the present invention be limited to the described embodiment. It is intended that the invention cover all alternatives, modifications, and equivalences which may be included within the spirit and scope of the invention.

Figure 1:
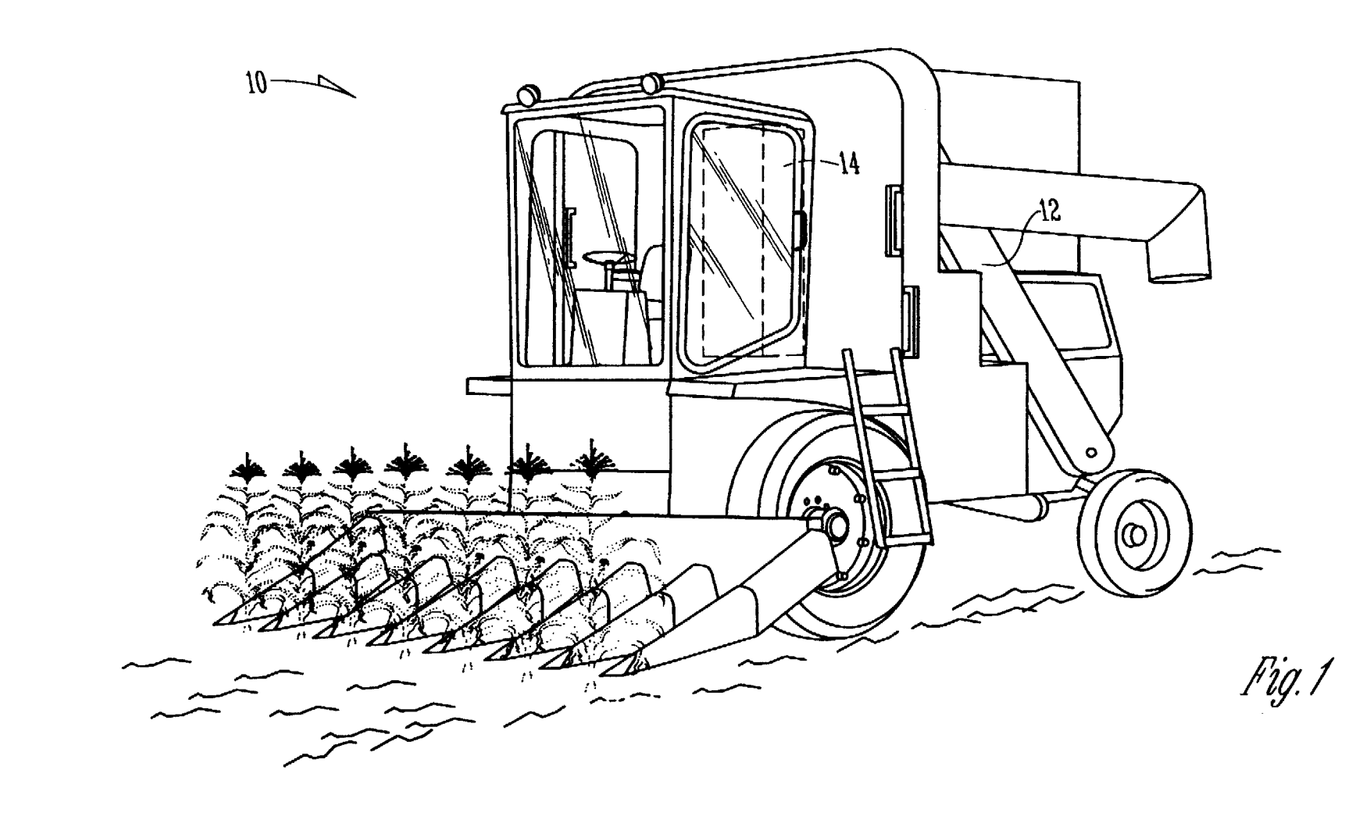
FIG. 1 is a perspective view of a research combine utilizing the present invention.

FIG. 1 shows a typical research combine 10 which may be used with the present invention. A research combine 10 is used by the plant hybrid industry to harvest test plots and to evaluate the harvested grain. The combine 10 is similar to a standard combine but is adapted to take samples of the grain from the test plots and analyze properties of the grain in the field. The combine 10 includes a sample elevator 12 which moves grain to a test chamber assembly 14 which is shown in detail in FIGS. 2 and 3.

Figure 2:
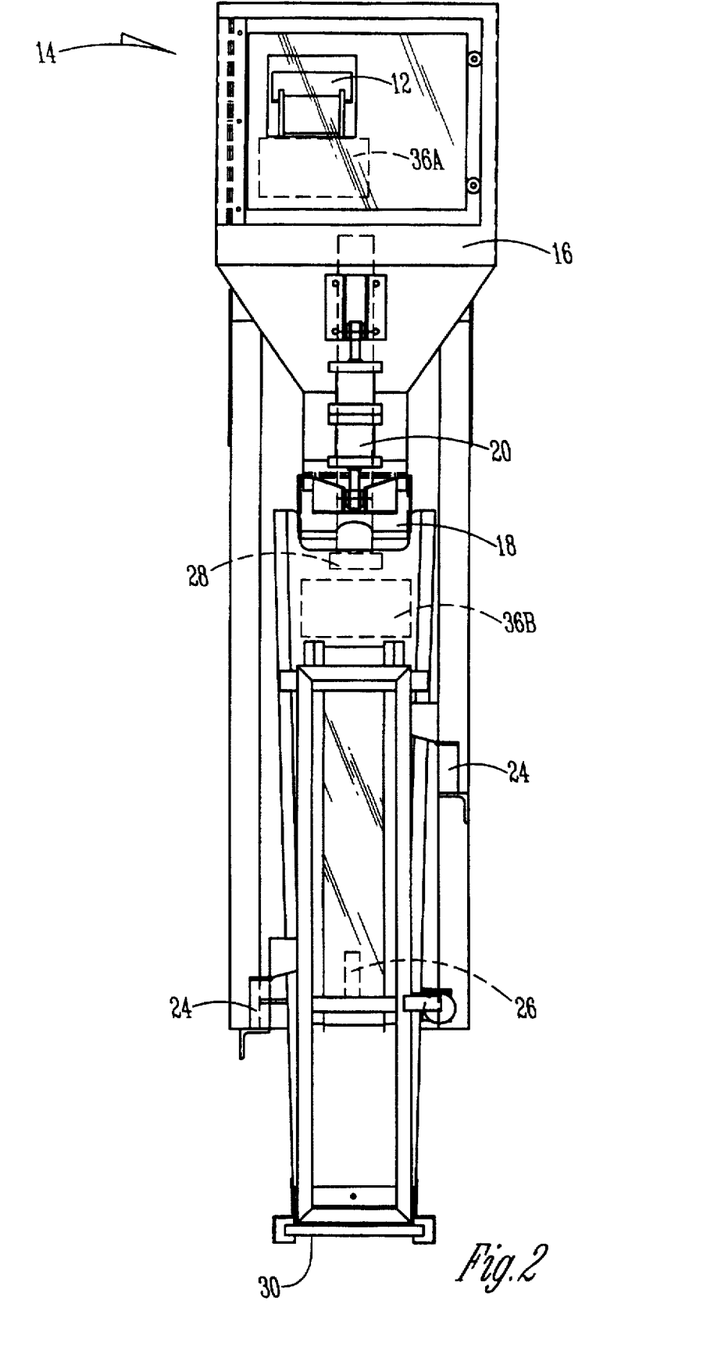
FIG. 2 is a front view of the test chamber assembly of the combine shown in FIG. 1.
Figure 3:
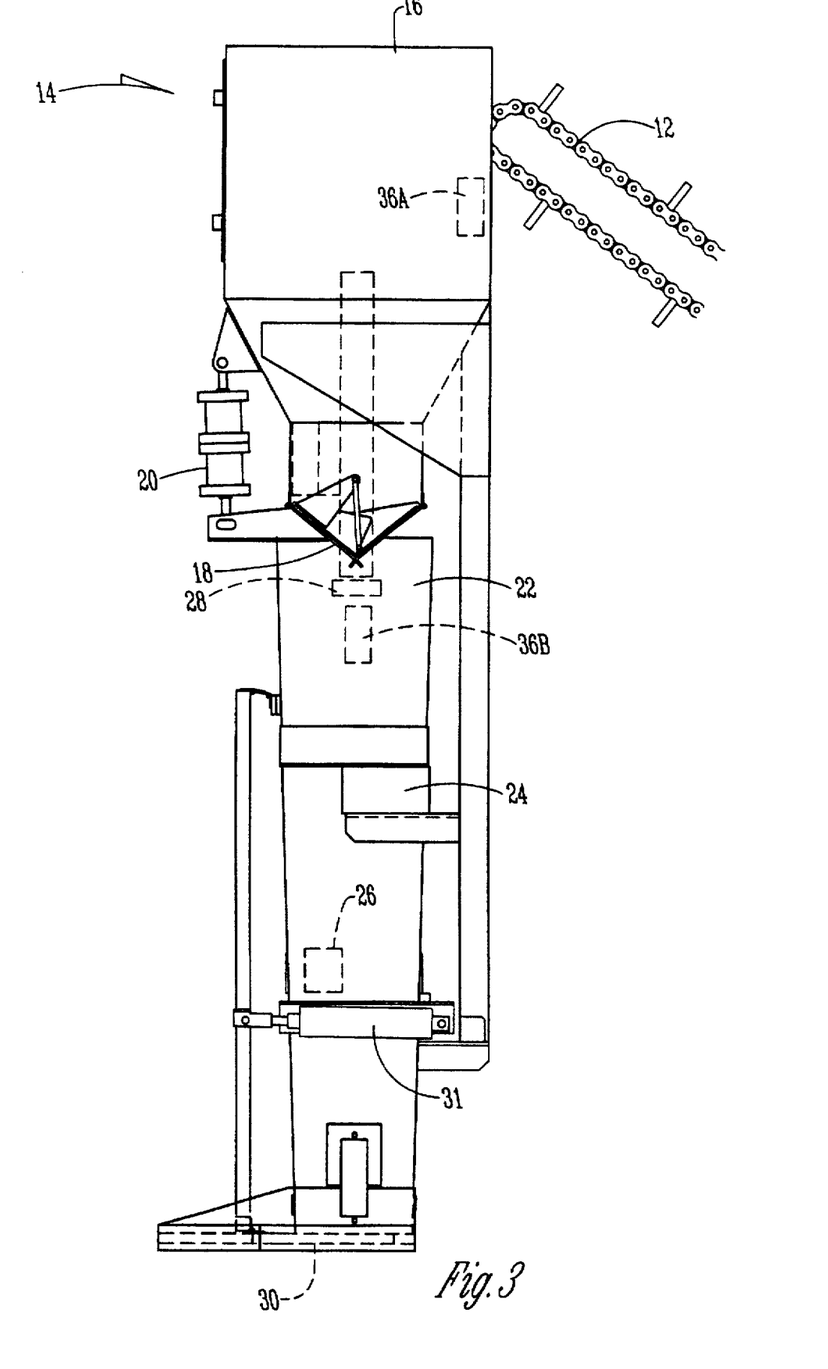
FIG. 3 is a side view of the test chamber assembly of the combine shown in FIG. 1.

The test chamber assembly 14 is designed to collect a sample of grain and to evaluate the grain to determine various properties of the grain. As shown in FIGS. 2 and 3, the grain enters the test chamber assembly 14 from the top from the elevator 12. After the grain falls off the elevator 12, it is collected in a chute 16. A door 18 prevents the grain from leaving the chute 16. The door 18 is controlled by a pneumatic door cylinder 20. The door 18 is controlled by the door cylinder 20 and moves from an opened to a closed position or any position in-between. When the door 18 is opened, the grain will fall into the test chamber 22. When the grain is in the test chamber 22, the sample is analyzed in a number of conventional ways. One or more load cells 24 are used to determine the weight of the grain within the chamber 22. A moisture sensor 26 is used to sense the moisture of the grain. A sonar device 28 is positioned above the chamber 22 and can determine how full the chamber is in order to determine the volume of grain in the chamber 22. Once these measurements are taken, an exit door 30 can be opened to empty the test chamber 22 so that a sample from the next test plot can be taken. The door 30 is controlled by an actuator 31 and its related linkages. A typical test plot of corn, for example, has two rows of corn each seventeen feet long. It takes the research combine 10 approximately fifteen seconds to harvest each test plot, so all the grain analysis must be completed within fifteen seconds.

Figure 4:
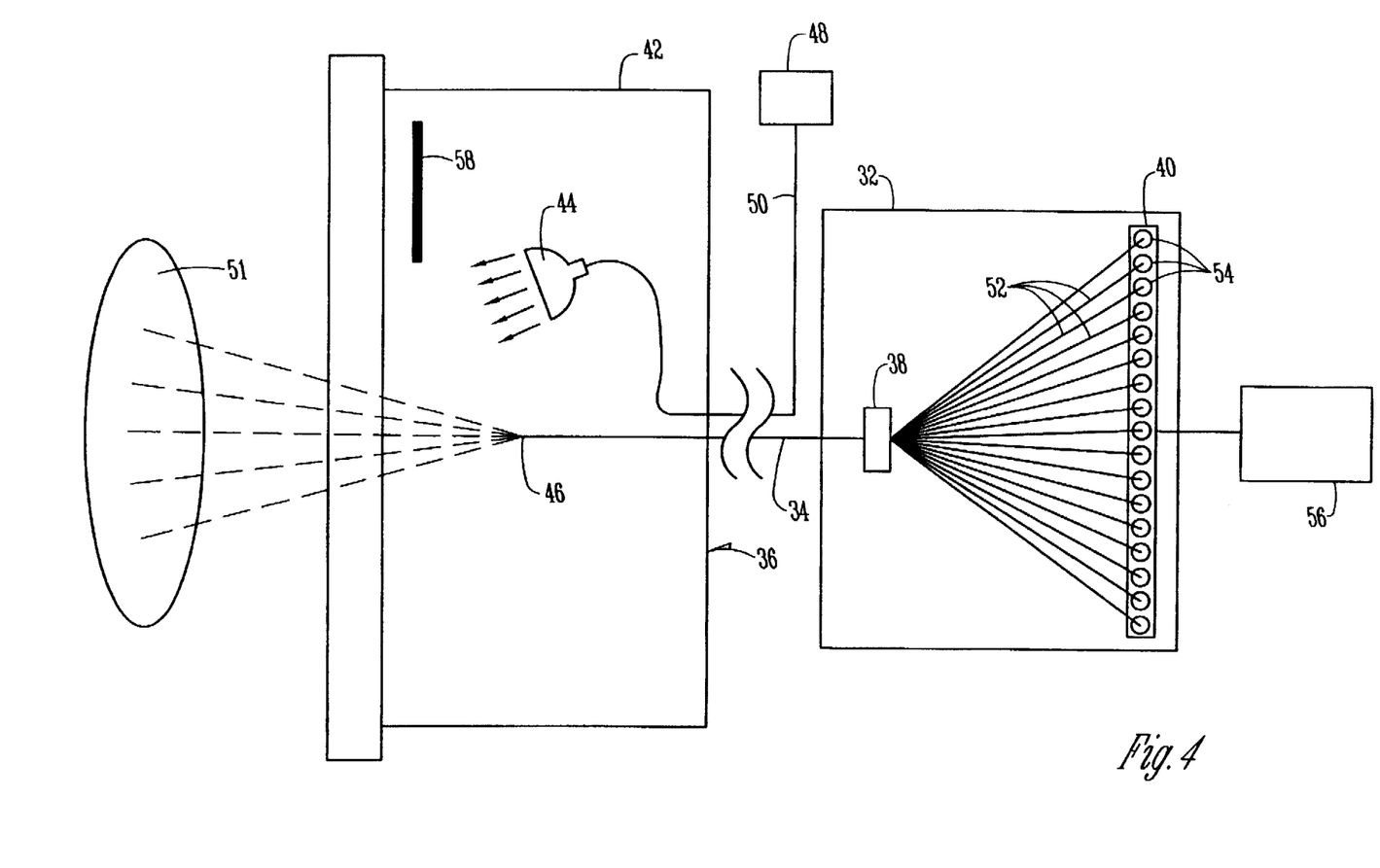
FIG. 4 is a block diagram of the present invention.

FIG. 4 is a block diagram of the present invention. FIG. 4 shows how the test chamber assembly 14 is used with the present invention. A monochromator 32, located in or near the cab of the combine 10, is connected to a fiber optic cable 34. The other end of the fiber optic cable 34 is connected to a sensor head 36. The sensor head 36 can be located in a number of locations relative to the test chamber assembly 14. FIGS. 2 and 3 show two possible locations for the sensor head 36. In a first location, a sensor head 36A is located below the elevator 12 and senses the grain as it falls into the chute 16. In a second location, a sensor head 36B is located below the chute 16 and the door 18 such that the grain is sensed as it falls through the door 18. At the second location, the amount of grain flowing past the sensor head 36B can be accurately controlled by controlling the amount that the door 18 is opened. Preferably, the area around the sensor head 36 is enclosed to limit the amount of stray light which effects the performance of the sensor head 36.

The monochromator 32 used with the present invention includes a fixed diffraction grating 38 and a photodiode array 40. It is important to note that because the photodiode array 40 is used, the monochromator 32 includes no moving optical parts. This is desired in order to withstand the extreme vibrations present in the environment of a combine. The photodiode array 40 also greatly increases the speed at which a sample can be analyzed since the entire desired spectrum of reflected light is transmitted at once, rather than scanning and transmitting one range at a time. The monochromator 32 is connected to a sensor head 36 by a bundle of fiber optic cables 34. While the fiber optic cable 34 could take on many forms, preferably the cable is comprised of 25 individual fiber optic strands.

Figure 5:
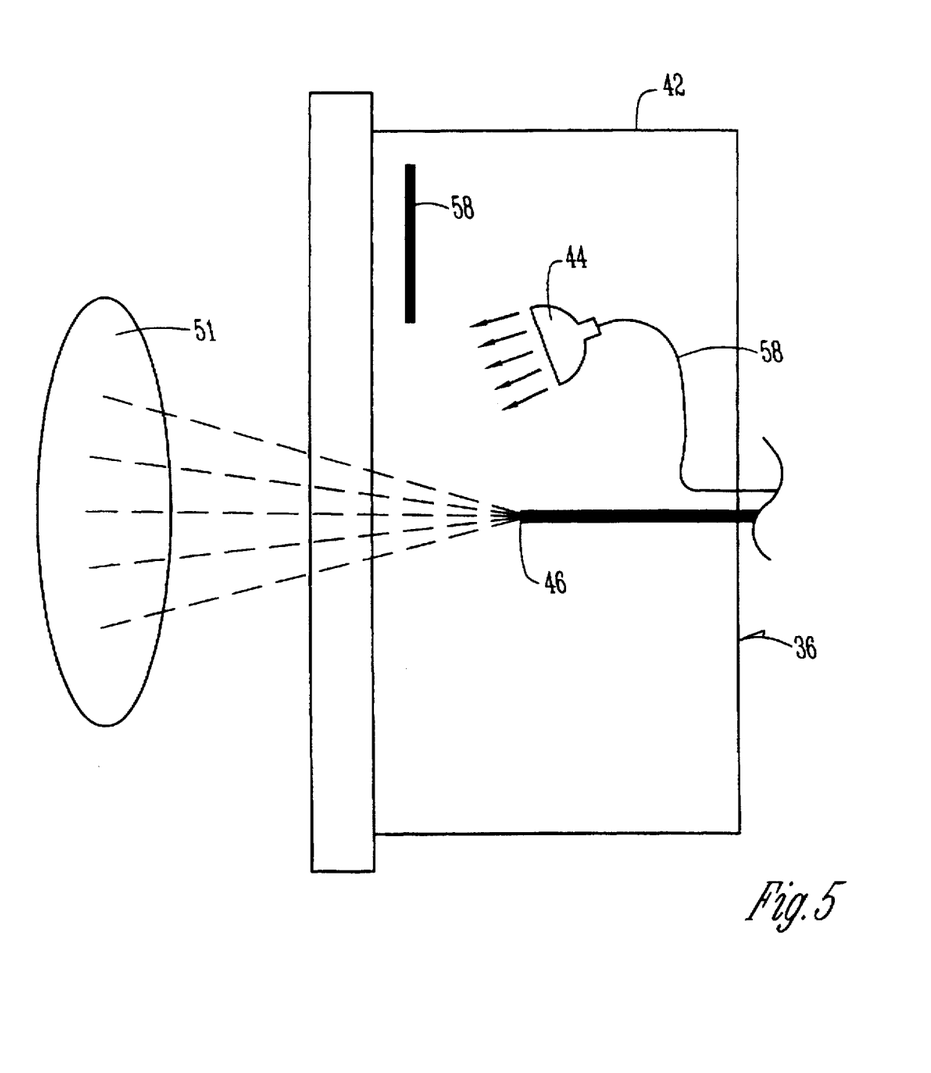
FIG. 5 is an enlarged view of the sensor head shown in FIG. 4.

FIG. 5 is an enlarged view of the sensor head 36. The sensor head 36 is comprised of a housing 42 which encloses a lamp 44 and a sensor 46. The sensor 46 could take on may forms, but preferably is simply comprised of the ends of the fiber optic strands of the fiber optic cable 34. The lamp is powered by a power source 48 (FIG. 4) which could be provided by the combine 10 or the monochromator 32. The power source is connected to the lamp 44 by a power cable 50 which is preferably bundled with the fiber optic cable 34 to reduce the number of cables between the sensor head 36 and the monochromator 32. The lamp 44 is preferably a halogen lamp which provides a wide spectrum of radiation including radiation in the desired bandwidth, 400 to 1100 nanometers (nm). The lamp 44 is aimed at a desired angle towards the grain samples (discussed below). FIG. 5 also shows a white reference tile 58. The white reference tile 58 has a known reflectance and therefore can be used to calibrate the present invention.

The light sensor 46 is also positioned at a desired location relative to the grain sample 51 and lamp 44 (discussed below). When the lamp 44 irradiates the grain sample with light, some of the radiation is reflected off the grain sample toward the sensor 46. The reflected light is transmitted through the fiber optic cable 34 to the diffraction grating 38 in the monochromator 32 (FIG. 4). The diffraction grating scatters the light over an infinite number of paths represented by lines 52. The photodiode array 40 includes 512 photo detectors 54 which are disposed along the photodiode array 40. For purposes of clarity in the drawings, all 512 photo detectors 54 are not shown. Each photo detector 54 will receive light from the diffraction grating over just a small range of wavelengths. The diffraction grating and photo detectors 54 are arranged in the monochromator 32 so that light with a spectral range of 400 through 1100 nanometers is distributed along the array 40. It can be seen that by using a photodiode array with 512 photo detectors 54, the "scanning" time goes down by a factor of 512 compared to the prior art scanning spectrometer. The photodiode array 40 is connected to a processor 56 which collects data from the photodiode array 40 and stores and analyzes the data.

The present invention improves on accuracy and speed over the prior art. To help improve accuracy of the system, the grain sample presentation is made constant and repeatable. This results in consistent results. The samples are sensed in the same way and in the same location for each successive sample. In a lab, lab technicians may not analyze different samples in exactly the same way. A more consistent result is obtained by automating the analyzation process. Also, sensing the samples as the grain is moving improves the accuracy and reliability since an "average" sample is taken, rather than looking at still kernels which have surfaces that vary from one part of the kernel to the other. Since the samples can be analyzed at a high rate of speed, the processor can average a number of readings to obtain a consistent result for each sample. For example, if the monochromator outputs spectrum data every 34 msec, then the processor can average 100 successive spectrums together and output a more reliable and stable spectrum every 3.4 seconds.

The present invention operates as follows. When harvesting a test plot, the research combine 10 harvests the grain in the test plot in a conventional manner. Referring to FIGS. 2 and 3, as grain from the harvested test plot enters the test chamber assembly 14 from the sample elevator 12, the chute 16 is filed with a sample of the grain. When the chamber 22 is ready for loading, the chute door 18 is opened by activating the door cylinder 20. The sensor head 36B of the present invention is located slightly below the door 18 and senses the grain as it flows past the sensor head 36B. The door 18 is opened a predetermined amount to allow an even flow of grain past the sensor head 36B. As the grain flows, past the sensor head 36, light from lamp 44 is irradiated on the grain sample with some of the light reflecting off the grain sample to the sensor 46 (FIG. 5). The reflected light is transmitted through the fiber optic bundle 34 to a diffraction grating 38 in the monochromator 32, which is located within or near the cab of the combine 10 (FIG. 4). The diffraction grating 38 spreads the reflected light over the photodiode array 40 in a spectrum ranging from approximately 400 nanometers to 1100 nm in wavelength. A processor 56 is connected to the photodiode array and collects data relating to the strength of radiation at each individual photodiode 54. By analyzing the strength of the radiation at each photodiode 54, the processor can determine the amount of constituents in the sample of grain. For example, if the radiation strength at a certain photodiode is relatively low, then it can be determined that the grain sample has absorbed an amount of radiation at that wavelength. By knowing what certain substances absorb or reflect, it can be determined what substances are present in the sample. The data collected from the monochromator 32 is processed by the processor 56 and/or stored for later use. Once all the grain from the chute 16 has fallen into the test chamber 22, the test assembly 14 will evaluate the grain for weight, moisture, volume, etc., using conventional methods as discussed above. In this way, the sample of grain from a given test plot can be thoroughly evaluated including the grain sample weight, moisture, volume, and amount of major constituents present.

As an alternative to using reflectance to measure constituents of a grain sample, light could be irradiated through the grain sample and sensed after being transmitted through the sample. Also, various geometries of lamps and sensors could be used. The lamps and sensors could also be separated into two or more components rather than being contained in a single component such as the sensor heads 36 shown in the Figures. The number of fiber optic strands in each embodiment could also vary greatly. Other types of radiation could be used with the present invention other than NIR. For example Fourier Transform IR (FTIR) could be used. Also, the diffraction grating 38 could be replaced with other elements for spreading the light in the monochromator.

The preferred embodiment of the present invention has been set forth in the drawings and specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

What is claimed is:

1. An apparatus for measuring constituents of harvested agricultural product on a combine comprising:
   monochromator mounted to the combine, the monochromator having no moving optical components;
   a device coupled to the combine for forming a flow of the harvested product past a sensing location;
   a radiation source coupled to the combine and disposed near the flow of harvested product for irradiating the product as the product flows past the sensing location;
   a fiber optic cable connected to the monochromator for transmitting radiation reflected off the agricultural product to the monochromator; and
   a data processor connected to the monochromator for identifying and determining the amount of constituents in the agricultural product.

2. The apparatus of claim 1 wherein the monochromator further comprises:
   a dispersive element immovably coupled to the monochromator; and
   a photodiode array immovably coupled to the monochromator for detecting radiation dispersed by the dispersive element.

3. The apparatus of claim 2 wherein the dispersive element is comprised of a diffraction grating.

4. The apparatus of claim 1 further comprising a sensor assembly coupled to the combine proximate the harvested product.

5. The apparatus of claim 4, wherein the sensor assembly further comprises:
   a frame mounted to the combine, wherein the radiation source is coupled to the frame, and wherein the fiber optic cable is coupled to the frame in a position which allows the fiber optic cable to receive reflected radiation from the product.

6. The apparatus of claim 5 wherein the radiation source is electrically connected to a power source on the combine by a power line, wherein the power line and the fiber optic cable are combined forming a cable assembly.

7. The apparatus of claim 5 wherein the fiber optic cable is further comprised of a plurality of fiber optic strands having first and second ends, wherein the first ends of the fiber optic strands form a radiation sensor.

8. The apparatus of claim 7 wherein the plurality of fiber optic strands are separated into a plurality of groups of strands, forming a plurality of radiation sensors.

9. The apparatus of claim 4 wherein the sensor assembly includes a housing.

10. The apparatus of claim 9 further comprising a reflective calibration surface disposed within the housing, wherein the reflective calibration surface is positioned where radiation from the radiation source is incident on the reflective calibration surface.

11. The apparatus of claim 1 further comprising a data storage device for storing data processed by the data processor.

12. The apparatus of claim 1, the device further comprising a door disposed below a source of harvested product and disposed above the sensing location, wherein the door can be selectively opened to form the flow of harvested product past the sensing location.

13. The apparatus of claim 12, wherein the rate of flow of harvested product past the sensing location can be adjusted by controlling the amount that the door is opened.

14. The apparatus of claim 12, wherein the door is controlled by a pneumatic door cylinder.

15. The apparatus of claim 1, the device further comprising an elevator disposed above the sensing location, wherein the harvested product flow downward from the elevator to form the flow of harvested product past the sensing location.

16. The apparatus of claim 1, wherein the harvested product is comprised of corn.

17. A method of measuring constituents of harvested agricultural product comprising the steps of:
   providing a combine for harvesting a field of crops (the agricultural product);
   providing a monochromator coupled to the combine, the monochromator including a photodiode array and a fixed dispersive element;
   providing a stream of moving the agricultural product within the combine;
   providing a radiation source coupled to the combine near the stream of moving product harvested by the combine;
   applying radiation to the stream of moving product;
   sensing radiation that is reflected off of the stream of moving product; and
   analyzing the sensed radiation to determine various constituents of the agricultural product.

18. The apparatus of claim 17, wherein the step of providing a stream of moving agricultural product within the combine further comprises the steps of:
   collecting a sample of the product in a chamber; and
   providing an aperture in the chamber for allowing the product to flow downward forming the stream of moving agricultural product.

19. The apparatus of claim 18, further comprising the step of providing a door for adjusting the size of the aperture in the chamber.

20. The apparatus of claim 17, further comprising the step of adjusting the rate of flow of the stream of agricultural product.

21. A method of analyzing on a combine an agricultural product harvested from a test plot comprising the steps of:
   harvesting the agricultural product with a research combine;

collecting a sample of the product and containing the sample in a chamber;

weighing the chamber to determine the weight of the sample;

sensing the moisture content of the sample in the chamber;

sensing the volume of the sample in the chamber; and determining the identity and amount of constituents in the sample, further comprising the steps of:
  allowing the sample of the product in the chamber to flow out of the chamber,
  irradiating the sample with radiation as it flows out of the chamber,
  sensing radiation which reflects off of the sample, and
  analyzing the spectrum of the reflected radiation to determine the identity and amount of constituents in the sample.

22. An apparatus for measuring constituents of harvested grain on a combine comprising:

a sensor coupled to the combine at a location proximate a flow of harvested grain;

a light source for irradiating the grain as the grain flows past the sensor, the light source being positioned such that light irradiated toward the grain is sensed by the sensor;

a monochromator having no moving optical components located in the combine, the monochromator being operatively connected to the sensor such that light sensed by the sensor is transmitted to the monochromator; and a processor operatively connected to the monochromator for identifying and determining the amount of constituents in the grain.

23. The apparatus of claim 22, wherein the light source is positioned such that the light is reflected off of the grain and sensed by the sensor.

24. The apparatus of claim 22, wherein the light source is positioned such that the light is transmitted through the grain and sensed by the sensor.

* * * * *

UNITED STATES PATENT AND TRADEMARK OFFICE
CERTIFICATE OF CORRECTION

PATENT NO. : 5,751,421  
DATED : May 12, 1998  
INVENTOR(S) : Steven L. Wright et al.

Page 1 of 1

It is certified that error appears in the above-identified patent and that said Letters Patent is hereby corrected as shown below:

Column 3,  
Line 39, replace "ANALYSES" with -- ANALYZES --.

Column 5,  
Line 24, replace "EFFECTS" with -- AFFECTS --.

Column 8,  
Line 51, replace "APPARATUS" with -- METHOD --.  
Line 58, replace "APPARATUS" with -- METHOD --.  
Line 61, replace "APPARATUS" with -- METHOD --.

Signed and Sealed this

Second Day of July, 2002

*Attest:*

JAMES E. ROGAN  
*Attesting Officer*  *Director of the United States Patent and Trademark Office*

(12) EX PARTE REEXAMINATION CERTIFICATE (10116th)
United States Patent
Wright et al.

(10) Number: US 5,751,421 C1
(45) Certificate Issued: Apr. 16, 2014

(54) NEAR INFRARED SPECTROMETER USED IN COMBINATION WITH A COMBINE FOR REAL TIME GRAIN ANALYSIS

(75) Inventors: Steven L. Wright, Johnston, IA (US); C. Fred Hood, Johnston, IA (US)

(73) Assignee: Textron Systems Corporation, Wilmington, MA (US)

Reexamination Request:
No. 90/020,022, Sep. 14, 2012

Reexamination Certificate for:
Patent No.: 5,751,421
Issued: May 12, 1998
Appl. No.: 08/807,661
Filed: Feb. 27, 1997

Certificate of Correction issued Jul. 2, 2002

(51) Int. Cl.
*G01J 3/28* (2006.01)
*A01F 12/00* (2006.01)

(52) U.S. Cl.
USPC .............................................. 356/328; 460/7

(58) Field of Classification Search
None
See application file for complete search history.

(56) References Cited

To view the complete listing of prior art documents cited during the proceeding for Reexamination Control Number 90/020,022, please refer to the USPTO's public Patent Application Information Retrieval (PAIR) system under the Display References tab.

*Primary Examiner* — Angela M Lie (57) ABSTRACT

An apparatus and method for combining NIR spectography with a combine for measuring major constituents of harvested grain in real time includes a monochromator having no moving optical parts. The monochromator includes a fixed diffraction grating and a photodiode collector comprised of a plurality of photodiodes. A radiation source irradiates a grain sample while a bundle of fiber optic strands transmits the reflected radiation to the diffraction grating. By analyzing the intensities and wavelengths of the reflected radiation at the photodiode collector, the presence and amount of major constituents of the harvested grain can be determined. The present invention may be used on a research combine along with the conventional instrumentation which measures the weight, moisture, and volume of grain harvested in a test plot.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 7, 8, 10, 12-14 and 24 is confirmed.

Claims 1-6, 9, 11, 15-23 are cancelled.

* * * * *